US008788001B2

(12) United States Patent
Li et al.

(10) Patent No.: US 8,788,001 B2
(45) Date of Patent: *Jul. 22, 2014

(54) TIME-DIVISION MULTIPLEXING IN A MULTI-WAVELENGTH PHOTON DENSITY WAVE SYSTEM

(75) Inventors: Youzhi Li, Longmont, CO (US); Andy S. Lin, Boulder, CO (US); Edward M. McKenna, Boulder, CO (US)

(73) Assignee: Covidien LP, Mansfield, MA (US)

( * ) Notice: Subject to any disclaimer, the term of this patent is extended or adjusted under 35 U.S.C. 154(b) by 907 days.

This patent is subject to a terminal disclaimer.

(21) Appl. No.: 12/563,852

(22) Filed: Sep. 21, 2009

(65) Prior Publication Data

US 2011/0071373 A1    Mar. 24, 2011

(51) Int. Cl.
*A61B 5/1455* (2006.01)
*A61B 6/00* (2006.01)

(52) U.S. Cl.
USPC ............ 600/310; 600/323; 600/473; 600/476

(58) Field of Classification Search
USPC ......... 600/310, 316, 322, 323, 326, 328, 330, 600/331, 338, 340, 342, 473, 476, 477; 356/41
See application file for complete search history.

(56) References Cited

U.S. PATENT DOCUMENTS

| | | |
|---|---|---|
| 3,638,640 A | 2/1972 | Shaw |
| 4,223,680 A | 9/1980 | Jöbsis |
| 4,281,645 A | 8/1981 | Jöbsis |
| 4,321,930 A | 3/1982 | Jöbsis et al. |
| 4,714,341 A | 12/1987 | Hamaguri et al. |
| 4,805,623 A | 2/1989 | Jöbsis |
| 4,807,631 A | 2/1989 | Hersh et al. |
| 4,911,167 A | 3/1990 | Corenman et al. |
| 4,913,150 A | 4/1990 | Cheung et al. |

(Continued)

FOREIGN PATENT DOCUMENTS

| | | |
|---|---|---|
| AU | 732799 B2 | 5/2001 |
| DE | 69123448 | 5/1997 |

(Continued)

OTHER PUBLICATIONS

International Search Report for PCT/US2010/046674 dated Apr. 26, 2011, 15 pgs.

(Continued)

*Primary Examiner* — Tse Chen
*Assistant Examiner* — Chu Chuan (JJ) Liu
(74) *Attorney, Agent, or Firm* — Fletcher Yoder, PC

(57) ABSTRACT

Multi-wavelength photon density wave medical systems, methods, and devices are provided. In one embodiment, a multi-wavelength system may include a sensor, a sensor cable, and a patient monitor. The sensor may have an emitter output and a detector input configured to pass a multi-wavelength photon density wave input signal into a patient and receive a resulting multi-wavelength photon density wave output signal. The sensor cable may couple to the sensor using two optical cables for transmitting and receiving the multi-wavelength photon density wave signals. The patient monitor may couple to the sensor cable and generate several time-division multiplexed single-wavelength input signals by modulating one or more light sources at a frequency sufficient to produce resolvable photon density waves. By combining the several time-division multiplexed single-wavelength input signals into one of the optical cables of the sensor cable, the patient monitor may generate the multi-wavelength photon density wave input signal.

19 Claims, 7 Drawing Sheets

(56) References Cited

U.S. PATENT DOCUMENTS

| | | | |
|---|---|---|---|
| 4,936,679 A | 6/1990 | Mersch | |
| 4,938,218 A | 7/1990 | Goodman et al. | |
| 4,971,062 A | 11/1990 | Hasebe et al. | |
| 4,972,331 A | 11/1990 | Chance | |
| 4,974,591 A | 12/1990 | Awazu et al. | |
| 5,028,787 A | 7/1991 | Rosenthal et al. | |
| 5,065,749 A | 11/1991 | Hasebe et al. | |
| 5,084,327 A | 1/1992 | Stengel | |
| 5,088,493 A | 2/1992 | Giannini et al. | |
| 5,119,815 A | 6/1992 | Chance | |
| 5,122,974 A | 6/1992 | Chance | |
| 5,167,230 A | 12/1992 | Chance | |
| 5,190,038 A | 3/1993 | Polson et al. | |
| 5,246,003 A | 9/1993 | DeLonzor | |
| 5,247,931 A | 9/1993 | Norwood | |
| 5,263,244 A | 11/1993 | Centa et al. | |
| 5,275,159 A | 1/1994 | Griebel | |
| 5,279,295 A | 1/1994 | Martens et al. | |
| 5,297,548 A | 3/1994 | Pologe | |
| 5,355,880 A | 10/1994 | Thomas et al. | |
| 5,372,136 A | 12/1994 | Steuer et al. | |
| 5,385,143 A | 1/1995 | Aoyagi | |
| 5,390,670 A | 2/1995 | Centa et al. | |
| 5,413,099 A | 5/1995 | Schmidt et al. | |
| 5,460,182 A * | 10/1995 | Goodman et al. | 600/473 |
| 5,469,845 A | 11/1995 | DeLonzor et al. | |
| 5,482,036 A | 1/1996 | Diab et al. | |
| 5,483,646 A | 1/1996 | Uchikoga | |
| 5,497,769 A | 3/1996 | Gratton et al. | |
| 5,553,614 A | 9/1996 | Chance | |
| 5,555,885 A | 9/1996 | Chance | |
| 5,564,417 A | 10/1996 | Chance | |
| 5,575,285 A | 11/1996 | Takanashi et al. | |
| 5,611,337 A | 3/1997 | Bukta | |
| 5,630,413 A | 5/1997 | Thomas et al. | |
| 5,645,059 A | 7/1997 | Fein et al. | |
| 5,645,060 A | 7/1997 | Yorkey | |
| 5,680,857 A | 10/1997 | Pelikan et al. | |
| 5,692,503 A | 12/1997 | Kuenstner | |
| 5,730,124 A | 3/1998 | Yamauchi | |
| 5,758,644 A | 6/1998 | Diab et al. | |
| 5,779,631 A | 7/1998 | Chance | |
| 5,782,757 A | 7/1998 | Diab et al. | |
| 5,786,592 A | 7/1998 | Hök | |
| 5,830,136 A | 11/1998 | DeLonzor et al. | |
| 5,830,139 A | 11/1998 | Abreu | |
| 5,831,598 A | 11/1998 | Kauffert et al. | |
| 5,842,981 A | 12/1998 | Larsen et al. | |
| 5,871,442 A | 2/1999 | Madarasz et al. | |
| 5,873,821 A | 2/1999 | Chance et al. | |
| 5,920,263 A | 7/1999 | Huttenhoff et al. | |
| 5,995,855 A | 11/1999 | Kiani et al. | |
| 5,995,856 A | 11/1999 | Mannheimer et al. | |
| 5,995,859 A | 11/1999 | Takahashi | |
| 6,011,986 A | 1/2000 | Diab et al. | |
| 6,064,898 A | 5/2000 | Aldrich | |
| 6,081,742 A | 6/2000 | Amano et al. | |
| 6,088,607 A | 7/2000 | Diab et al. | |
| 6,095,974 A * | 8/2000 | Shemwell et al. | 600/310 |
| 6,120,460 A | 9/2000 | Abreu | |
| 6,122,042 A | 9/2000 | Wonderman et al. | |
| 6,134,460 A | 10/2000 | Chance | |
| 6,150,951 A | 11/2000 | Olejniczak | |
| 6,154,667 A | 11/2000 | Miura et al. | |
| 6,163,715 A | 12/2000 | Larsen et al. | |
| 6,181,958 B1 | 1/2001 | Steuer et al. | |
| 6,181,959 B1 | 1/2001 | Schöllermann et al. | |
| 6,192,260 B1 | 2/2001 | Chance | |
| 6,192,261 B1 | 2/2001 | Gratton et al. | |
| 6,230,035 B1 | 5/2001 | Aoyagi et al. | |
| 6,266,546 B1 | 7/2001 | Steuer et al. | |
| 6,285,895 B1 | 9/2001 | Ristolainen et al. | |
| 6,312,393 B1 | 11/2001 | Abreu | |
| 6,322,515 B1 | 11/2001 | Goor et al. | |
| 6,352,502 B1 | 3/2002 | Chaiken et al. | |
| 6,353,750 B1 | 3/2002 | Kimura et al. | |
| 6,397,091 B2 | 5/2002 | Diab et al. | |
| 6,415,236 B2 | 7/2002 | Kobayashi et al. | |
| 6,419,671 B1 | 7/2002 | Lemberg | |
| 6,438,399 B1 | 8/2002 | Kurth | |
| 6,453,183 B1 * | 9/2002 | Walker | 600/322 |
| 6,461,305 B1 | 10/2002 | Schnall | |
| 6,466,809 B1 | 10/2002 | Riley | |
| 6,487,439 B1 | 11/2002 | Skladnev et al. | |
| 6,501,974 B2 | 12/2002 | Huiku | |
| 6,501,975 B2 | 12/2002 | Diab et al. | |
| 6,516,209 B2 | 2/2003 | Cheng et al. | |
| 6,526,301 B2 | 2/2003 | Larsen et al. | |
| 6,544,193 B2 | 4/2003 | Abreu | |
| 6,546,267 B1 | 4/2003 | Sugiura et al. | |
| 6,549,795 B1 | 4/2003 | Chance | |
| 6,553,242 B1 * | 4/2003 | Sarussi | 600/323 |
| 6,580,086 B1 | 6/2003 | Schulz et al. | |
| 6,591,122 B2 | 7/2003 | Schmitt | |
| 6,594,513 B1 | 7/2003 | Jobsis et al. | |
| 6,606,509 B2 | 8/2003 | Schmitt | |
| 6,606,511 B1 | 8/2003 | Ali et al. | |
| 6,615,064 B1 | 9/2003 | Aldrich | |
| 6,618,042 B1 | 9/2003 | Powell | |
| 6,622,095 B2 | 9/2003 | Kobayashi et al. | |
| 6,654,621 B2 | 11/2003 | Palatnik et al. | |
| 6,654,624 B2 | 11/2003 | Diab et al. | |
| 6,658,276 B2 | 12/2003 | Kianl et al. | |
| 6,658,277 B2 | 12/2003 | Wasserman | |
| 6,662,030 B2 | 12/2003 | Khalil et al. | |
| 6,668,183 B2 | 12/2003 | Hicks et al. | |
| 6,671,526 B1 | 12/2003 | Aoyagi et al. | |
| 6,671,528 B2 | 12/2003 | Steuer et al. | |
| 6,678,543 B2 | 1/2004 | Diab et al. | |
| 6,684,090 B2 | 1/2004 | Ali et al. | |
| 6,690,958 B1 | 2/2004 | Walker et al. | |
| 6,697,658 B2 | 2/2004 | Al-Ali | |
| 6,708,048 B1 | 3/2004 | Chance | |
| 6,711,424 B1 | 3/2004 | Fine et al. | |
| 6,711,425 B1 | 3/2004 | Reuss | |
| 6,714,245 B1 | 3/2004 | Ono | |
| 6,731,274 B2 | 5/2004 | Powell | |
| 6,785,568 B2 | 8/2004 | Chance | |
| 6,793,654 B2 | 9/2004 | Lemberg | |
| 6,801,648 B2 | 10/2004 | Cheng | |
| 6,801,797 B2 | 10/2004 | Mannheimer et al. | |
| 6,801,798 B2 | 10/2004 | Geddes et al. | |
| 6,801,799 B2 | 10/2004 | Mendelson | |
| 6,829,496 B2 | 12/2004 | Nagai et al. | |
| 6,850,053 B2 | 2/2005 | Daalmans et al. | |
| 6,859,658 B1 | 2/2005 | Krug | |
| 6,863,652 B2 | 3/2005 | Huang et al. | |
| 6,873,865 B2 | 3/2005 | Steuer et al. | |
| 6,889,153 B2 | 5/2005 | Dietiker | |
| 6,898,451 B2 | 5/2005 | Wuori | |
| 6,939,307 B1 | 9/2005 | Dunlop | |
| 6,947,780 B2 | 9/2005 | Scharf | |
| 6,949,081 B1 | 9/2005 | Chance | |
| 6,961,598 B2 | 11/2005 | Diab | |
| 6,983,178 B2 | 1/2006 | Fine et al. | |
| 6,993,371 B2 | 1/2006 | Kiani et al. | |
| 6,996,427 B2 | 2/2006 | Ali et al. | |
| 7,006,676 B1 | 2/2006 | Zeylikovich et al. | |
| 7,024,235 B2 | 4/2006 | Melker et al. | |
| 7,027,849 B2 | 4/2006 | Al-Ali | |
| 7,030,749 B2 | 4/2006 | Al-Ali | |
| 7,035,697 B1 | 4/2006 | Brown | |
| 7,047,056 B2 | 5/2006 | Hannula et al. | |
| 7,090,648 B2 | 8/2006 | Sackner et al. | |
| 7,127,278 B2 | 10/2006 | Melker et al. | |
| 7,162,306 B2 | 1/2007 | Caby et al. | |
| 7,164,938 B2 | 1/2007 | Geddes et al. | |
| 7,209,775 B2 | 4/2007 | Bae et al. | |
| 7,236,811 B2 | 6/2007 | Schmitt | |
| 7,263,395 B2 | 8/2007 | Chan et al. | |
| 7,272,426 B2 | 9/2007 | Schmid | |
| 7,330,746 B2 | 2/2008 | Demuth et al. | |
| 7,373,193 B2 | 5/2008 | Al-Ali et al. | |
| 7,375,347 B2 | 5/2008 | Colvin et al. | |

(56) References Cited

U.S. PATENT DOCUMENTS

| | | | |
|---|---|---|---|
| 7,378,954 | B2 | 5/2008 | Wendt |
| 2001/0005773 | A1 | 6/2001 | Larsen et al. |
| 2001/0020122 | A1 | 9/2001 | Steuer et al. |
| 2001/0039376 | A1 | 11/2001 | Steuer et al. |
| 2001/0044700 | A1 | 11/2001 | Kobayashi et al. |
| 2002/0026106 | A1 | 2/2002 | Khalil et al. |
| 2002/0035318 | A1 | 3/2002 | Mannheimer et al. |
| 2002/0038079 | A1 | 3/2002 | Steuer et al. |
| 2002/0042558 | A1 | 4/2002 | Mendelson |
| 2002/0049389 | A1 | 4/2002 | Abreu |
| 2002/0062071 | A1 | 5/2002 | Diab et al. |
| 2002/0111748 | A1 | 8/2002 | Kobayashi et al. |
| 2002/0133068 | A1 | 9/2002 | Huiku |
| 2002/0147400 | A1 | 10/2002 | Chance |
| 2002/0156354 | A1 | 10/2002 | Larson |
| 2002/0161287 | A1 | 10/2002 | Schmitt |
| 2002/0161290 | A1 | 10/2002 | Chance |
| 2002/0165439 | A1 | 11/2002 | Schmitt |
| 2002/0198443 | A1 | 12/2002 | Ting |
| 2003/0023140 | A1 | 1/2003 | Chance |
| 2003/0055324 | A1 | 3/2003 | Wasserman |
| 2003/0060693 | A1 | 3/2003 | Monfre et al. |
| 2003/0139687 | A1 | 7/2003 | Abreu |
| 2003/0144584 | A1 | 7/2003 | Mendelson |
| 2003/0220548 | A1 | 11/2003 | Schmitt |
| 2003/0220576 | A1 | 11/2003 | Diab |
| 2004/0010188 | A1 | 1/2004 | Wasserman |
| 2004/0054270 | A1 | 3/2004 | Pewzner et al. |
| 2004/0087846 | A1 | 5/2004 | Wasserman |
| 2004/0107065 | A1 | 6/2004 | Al-Ali |
| 2004/0127779 | A1 | 7/2004 | Steuer et al. |
| 2004/0171920 | A1 | 9/2004 | Mannheimer et al. |
| 2004/0176670 | A1 | 9/2004 | Takamura et al. |
| 2004/0176671 | A1 | 9/2004 | Fine et al. |
| 2004/0230106 | A1 | 11/2004 | Schmitt et al. |
| 2005/0080323 | A1 | 4/2005 | Kato |
| 2005/0101850 | A1 | 5/2005 | Parker |
| 2005/0113651 | A1 | 5/2005 | Wood et al. |
| 2005/0113656 | A1 | 5/2005 | Chance |
| 2005/0168722 | A1 | 8/2005 | Forstner et al. |
| 2005/0177034 | A1 | 8/2005 | Beaumont |
| 2005/0192488 | A1 | 9/2005 | Bryenton et al. |
| 2005/0203357 | A1 | 9/2005 | Debreczeny et al. |
| 2005/0209516 | A1 | 9/2005 | Fraden |
| 2005/0228248 | A1 | 10/2005 | Dietiker |
| 2005/0267346 | A1 | 12/2005 | Faber et al. |
| 2005/0283059 | A1 | 12/2005 | Iyer et al. |
| 2006/0009688 | A1 | 1/2006 | Lamego et al. |
| 2006/0015021 | A1 | 1/2006 | Cheng |
| 2006/0020181 | A1 | 1/2006 | Schmitt |
| 2006/0030763 | A1 | 2/2006 | Mannheimer et al. |
| 2006/0052680 | A1 | 3/2006 | Diab |
| 2006/0058595 | A1 | 3/2006 | Herrmann |
| 2006/0058683 | A1 | 3/2006 | Chance |
| 2006/0063995 | A1 | 3/2006 | Yodh et al. |
| 2006/0064024 | A1 | 3/2006 | Schnall |
| 2006/0122475 | A1 | 6/2006 | Balberg et al. |
| 2006/0129037 | A1 | 6/2006 | Kaufman et al. |
| 2006/0129038 | A1 | 6/2006 | Zelenchuk et al. |
| 2006/0195028 | A1 | 8/2006 | Hannula et al. |
| 2006/0224058 | A1 | 10/2006 | Mannheimer |
| 2006/0247501 | A1 | 11/2006 | Ali |
| 2006/0247506 | A1 | 11/2006 | Balberg et al. |
| 2006/0258921 | A1 | 11/2006 | Addison et al. |
| 2007/0093702 | A1 | 4/2007 | Yu et al. |
| 2008/0139908 | A1 | 6/2008 | Kurth |
| 2008/0200823 | A1 | 8/2008 | Cho et al. |
| 2008/0220512 | A1 | 9/2008 | Koh et al. |
| 2008/0312533 | A1 | 12/2008 | Balberg et al. |

FOREIGN PATENT DOCUMENTS

| | | |
|---|---|---|
| DE | 19640807 | 9/1997 |
| EP | 0194105 | 9/1986 |
| JP | 3124073 | 5/1991 |
| JP | 3170866 | 7/1991 |
| JP | 3238813 | 10/1991 |
| JP | 4191642 | 7/1992 |
| JP | 4332536 | 11/1992 |
| JP | 5049624 | 3/1993 |
| JP | 7124138 | 5/1995 |
| JP | 10216115 | 9/1998 |
| JP | 11019074 | 1/1999 |
| JP | 2003194714 | 7/2003 |
| JP | 2003210438 | 7/2003 |
| JP | 2003275192 | 9/2003 |
| JP | 2003339678 | 12/2003 |
| JP | 2004008572 | 1/2004 |
| JP | 2004194908 | 7/2004 |
| JP | 2004202190 | 7/2004 |
| JP | 2004248819 | 9/2004 |
| JP | 2004290544 | 10/2004 |
| JP | 2004290545 | 10/2004 |
| WO | WO9101678 | 2/1991 |
| WO | WO9200513 | 1/1992 |
| WO | WO9221281 | 12/1992 |
| WO | WO9309711 | 5/1993 |
| WO | WO9313706 A2 | 7/1993 |
| WO | WO93/16629 | 9/1993 |
| WO | WO9403102 | 2/1994 |
| WO | WO9512349 | 5/1995 |
| WO | WO9749330 | 12/1997 |
| WO | WO9817174 | 5/1998 |
| WO | WO98/42249 | 10/1998 |
| WO | WO98/42251 | 10/1998 |
| WO | WO9843071 | 10/1998 |
| WO | WO9932030 | 7/1999 |
| WO | WO0021438 | 4/2000 |
| WO | WO0140776 | 6/2001 |
| WO | WO03077750 | 9/2003 |
| WO | WO2004010844 | 2/2004 |
| WO | WO2005009221 | 2/2005 |
| WO | WO2005064314 A1 | 7/2005 |
| WO | WO2007051066 | 5/2007 |

OTHER PUBLICATIONS

D.J. Pine, et al.; "Diffusing-Wave Spectroscopy," *The American Physical Society*, vol. 60, No. 12, Mar. 1988, pp. 1134-1137.

D.J. Pine, et al.; "Diffusing-wave spectroscopy: dynamic light scattering in the multiple scattering limit," *J. Phys. France*, vol. 51, Sep. 1990, pp. 2101-2127.

X.L. Wu, et al.; "Diffusing-wave spectroscopy in a shear flow," *J. Opt. Soc. Am. B.*, vol. 7, No. 1, Jan. 1990, pp. 15-20.

J.M. Schmitt, et al.; "Interference of diffusive light waves," *J. Opt. Soc. Am. A.*, vol. 9, No. 10 (Oct. 1992), pp. 1832-1843.

Aoyagi, T., et al.; "Analysis of Motion Artifacts in Pulse Oximetry," Japanese Society ME, vol. 42, p. 20 (1993) (Article in Japanese—contains English summary of article).

D.A. Weitz, et al.; "Diffusing-Wave Spectroscopy: The Technique and Some Applications," *Physica Scripta*, vol. T49, 1993, pp. 610-621.

Barreto, A.B., et al.; "Adaptive Cancelation of Motion artifact in Photoplethysmographic Blood Volume Pulse Measurements for Exercise Evaluation," IEEE-EMBC and CMBEC—Theme 4: Signal Processing, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," Journal of clinical Monitoring, vol. 13, pp. 109-113 (1997).

Barnum, P.T., et al.; "Novel Pulse Oximetry Technology Capable of Reliable Bradycardia Monitoring in the Neonate," Respiratory Care, vol. 42, No. 1, p. 1072 (Nov. 1997).

Poets, C. F., et al.; "Detection of movement artifact in recorded pulse oximeter saturation," Eur. J. Pediatr.; vol. 156, pp. 808-811 (1997).

Masin, Donald I., et al.; "Fetal Transmission Pulse Oximetry," Proceedings 19th International Conference IEEE/EMBS, Oct. 30-Nov. 2, 1997; pp. 2326-2329.

(56) References Cited

OTHER PUBLICATIONS

Nijland, Roel, et al.; "Validation of Reflectance Pulse Oximetry: An Evaluation of a new Sensor in Piglets," Journal of Clinical Monitoring, vol. 13, pp. 43-49 (1997).
Nogawa, Masamichi, et al.; "A New Hybrid Reflectance Optical Pulse Oximetry Sensor for Lower Oxygen Saturation Measurement and for Broader Clinical Application," SPIE, vol. 2976, pp. 78-87 (1997).
Mannheimer, Paul D., et al.; "Wavelength Selection for Low-Saturation Pulse Oximetry," IEEE Transactions on Biomedical Engineering, vol. 44, No. 3, pp. 148-158 (Mar. 1997).
Buschman, J.P., et al.; "Principles and Problems of Calibration of Fetal Oximeters," Biomedizinische Technik, vol. 42, pp. 265-266 (1997).
Leahy, Martin J., et al.; "Sensor Validation in Biomedical Applications," IFAC Modelling and Control in Biomedical Systems, Warwick, UK; pp. 221-226 (1997).
Barreto, Armando B., et al.; "Adaptive LMS Delay Measurement in dual Blood Volume Pulse Signals for Non-Invasive Monitoring," IEEE, pp. 117-120 (1997).
East, Christine E., et al.; "Fetal Oxygen Saturation and Uterine Contractions During Labor," American Journal of Perinatology, vol. 15, No. 6, pp. 345-349 (Jun. 1998).
Hayes, Matthew J., et al.; "Quantitative evaluation of photoplethysmographic artifact reduction for pulse oximetry," SPIE, vol. 3570, pp. 138-147 (Sep. 1998).
Edrich, Thomas, et al.; "Can the Blood Content of the Tissues be Determined Optically During Pulse Oximetry Without Knowledge of the Oxygen Saturation?—An In-Vitro Investigation," Proceedings of the 20th Annual International conference of the IEEE Engie in Medicine and Biology Society, vol. 20, No. 6, p. 3072-3075, 1998.
Hayes, Matthew J., et al.; "Artifact reduction in photoplethysmography," Applied Optics, vol. 37, No. 31, pp. 7437-7446 (Nov. 1998).
S.E. Skipetrov, et al.; "Diffusing-wave spectroscopy in randomly inhomogeneous media with spatially localized scatterer flows," *Journal of Experimental and Theoretical Physics*, vol. 86, No. 4, Apr. 1998, pp. 661-665.
Such, Hans Olaf; "Optoelectronic Non-invasive Vascular Diagnostics Using multiple Wavelength and Imaging Approach," Dissertation, (1998).
Lutter, N., et al.; "Comparison of Different Evaluation Methods for a Multi-wavelength Pulse Oximeter," Biomedizinische Technik, vol. 43, (1998).
Z.L. Wu, et al.; "Laser modulated scattering as a nondestructive evaluation tool for defect inspection in optical materials for high power laser applications," *Optics Express*, vol. 3, No. 10; Nov. 1998, pp. 376-383.
Todd, Bryan, et al.; "The Identification of Peaks in Physiological Signals," Computers and Biomedical Research, vol. 32, pp. 322-335 (1999).
G. Popescu, et al.; "Optical path-length spectroscopy of wave propagation in random media," *Optics Letters*, vol. 24, No. 7, Apr. 1999, pp. 442-444.
Rhee, Sokwoo, et al.; "Design of a Artifact-Free Wearable Plethysmographic Sensor," Proceedings of the First joint BMES/EMBS Conference, Oct. 13-16, 1999, Altanta, Georgia, p. 786.
Rheineck-Leyssius, Aart t., et al.; "Advanced Pulse Oximeter Signal Processing Technology Compared to Simple Averaging: I. Effect on Frequency of Alarms in the Operating Room," Journal of clinical Anestesia, vol. 11, pp. 192-195 (1999).
Kaestle, S.; "An Algorithm for Reliable Processing of Pulse Oximetry Signals Under strong Noise Conditions," Dissertation Book, Lubeck University, Germany (1999).
Seelbach-Göbel, Birgit, et al.; "The prediction of fetal acidosis by means of intrapartum fetal pulse oximetry," Am J. Obstet. Gynecol., vol. 180, No. 1, Part 1, pp. 73-81 (1999).
Goldman, Julian M.; "Masimo Signal Extraction Pulse Oximetry," Journal of Clinical Monitoring and Computing, vol. 16, pp. 475-483 (2000).
Coetzee, Frans M.; "Noise-Resistant Pulse Oximetry Using a Synthetic Reference Signal," IEEE Transactions on Biomedical Engineering, vol. 47, No. 8, Aug. 2000, pp. 1018-1026.
Al. N. Korolevich, et al.: "Experimental study of the potential use of diffusing wave spectroscopy to investigate the structural characteristics of blood under multiple scattering," *Bioelectrochemistry*, vol. 52, 2000, pp. 223-227.
V. Ntziachristos, et al.; "Oximetry based on diffuse photon density wave differentials," *Am. Assoc. Phys. Med.*, vol. 27, No. 2, Feb. 2000, pp. 410-521.
Yao, Jianchu, et al.; "Design of a Plug-and-Play Pulse Oximeter," Proceedings of the Second Joint EMBS/BMES Conference, Houston, Texas, Oct. 23-26, 2002; pp. 1752-1753.
Kaestle, S.; "Determining Artefact Sensitivity of New Pulse Oximeters in Laboratory Using Signals Obtained from Patient," Biomedizinische Technik, vol. 45 (2000).
Cysewska-Sobusaik, Anna; "Metrological Problems With noninvasive Transillumination of Living Tissues," Proceedings of SPIE, vol. 4515, pp. 15-24 (2001).
Belal, Suliman Yousef, et al.; "A fuzzy system for detecting distorted plethysmogram pulses in neonates and paediatric patients," Physiol. Meas., vol. 22, pp. 397-412 (2001).
Hayes, Matthew J., et al.; "A New Method for Pulse Oximetry Possessing Inherent Insensitivity to Artifact," IEEE Transactions on Biomedical Engineering, vol. 48, No. 4, pp. 452-461 (Apr. 2001).
Maletras, Francois-Xavier, et al.; "Construction and calibration of a new design of Fiber Optic Respiratory Plethysmograph (FORP)," Optomechanical Design and Engineering, Proceedings of SPIE, vol. 4444, pp. 285-293 (2001).
Gehring, Harmut, et al.; "The Effects of Motion Artifact and Low Perfusion on the Performance of a New Generation of Pulse Oximeters in Volunteers Undergoing Hypoxemia," Respiratory Care, Vo. 47, No. 1, pp. 48-60 (Jan. 2002).
Jopling, Michae W., et al.; "Issues in the Laboratory Evaluation of Pulse Oximeter Performance," Anesth Analg, vol. 94, pp. S62-S68 (2002).
Lutter, N., et al.; "Accuracy of Noninvasive Continuous Blood Pressure; Measurement Utilising the Pulse Transit Time," Journal of clinical Monitoring and Computing, vol. 17, Nos. 7-8, pp. 469 (2002).
Gostt, R., et al.; "Pulse Oximetry Artifact Recognition Algorithm for Computerized Anaesthetic Records," Journal of Clinical Monitoring and Computing Abstracts, p. 471 (2002).
Chan, K.W., et al.; "17.3: Adaptive Reduction of Motion Artifact from Photoplethysmographic Recordings using a Variable Step-Size LMS Filter," IEEE, pp. 1343-1346 (2002).
Yamaya, Yoshiki, et al.; "Validity of pulse oximetry during maximal exercise in normoxia, hypoxia, and hyperoxia," J. Appl. Physiol., vol. 92, pp. 162-168 (2002).
Relente, A.R., et al.; "Characterization and Adaptive Filtering of Motion Artifacts in Pulse Oximetry using Accelerometers," Proceedings of the Second joint EMBS/BMES Conference, Houston, Texas, Oct. 23-26, 2002; pp. 1769-1770.
Yoon, Gilwon, et al.; Multiple diagnosis based on Photoplethysmography: hematocrit, SpO2, pulse and respiration, Optics in Health Care and Biomedical optics: Diagnostics and Treatment; Proceedings of the SPIE, vol. 4916; pp. 185-188 (2002).
Tremper, K.K.; "A Second Generation Technique for Evaluating Accuracy and Reliability of Second Generation Pulse Oximeters," Journal of Clinical Monitoring and Computing, vol. 16, pp. 473-474 (2000).
Lopez-Silva, Sonnia Maria Lopez, et al.; "Near-infrared transmittance pulse oximetry with laser diodes," Journal of Biomedical Optics, vol. 8, No. 3, pp. 525-533 (Jul. 2003).
Cyrill, D., et al.; "Adaptive Comb Filter for Quasi-Periodic Physiologic Signals," Proceedings of the 25th Annual International Conference of the IEEE EMBS, Cancun, Mexico, Sep. 17-21, 2003; pp. 2439-2442.
Stetson, Paul F.; "Determining Heart Rate from Noisey Pulse Oximeter Signals Using Fuzzy Logic," The IEEE International Conference on Fuzzy Systems, St. Louis, Missouri, May 25-28, 2003; pp. 1053-1058.

(56) References Cited

OTHER PUBLICATIONS

Aoyagi, Takuo; "Pulse oximetry: its invention, theory, and future," Journal of Anesthesia, vol. 17, pp. 259-266 (2003).

Lee, C.M., et al.; "Reduction of motion artifacts from photoplethysmographic recordings using wavelet denoising approach," IEEE EMBS Asian-Pacific Conference on Biomedical Engineering, Oct. 20-22, 2003; pp. 194-195.

A. Johansson; "Neural network for photoplethysmographic respiratory rate monitoring," Medical & Biological Engineering & Computing, vol. 41, pp. 242-248 (2003).

Lopez-Silva, S.M., et al.; "Transmittance Photoplethysmography and Pulse Oximetry With Near Infrared Laser Diodes," IMTC 2004—Instrumentation and Measurement Technology Conference, Como, Italy, May 18-20, 2004; pp. 718-723.

Addison, Paul S., et al.; "A novel time-frequency-based 3D Lissajous figure method and its application to the determination of oxygen saturation from the photoplethysmogram," Institute of Physic Publishing, Meas. Sci. Technol., vol. 15, pp. L15-L18 (2004).

Yao, Jianchu, et al.; "A Novel Algorithm to Separate Motion Artifacts from Photoplethysmographic Signals Obtained With a Reflectance Pulse Oximeter," Proceedings of the 26th Annual International conference of the IEEE EMBS, San Francisco, California, Sep. 2004, pp. 2153-2156.

Matsuzawa, Y., et al.; "Pulse Oximeter," Home Care Medicine, pp. 42-45 (Jul. 2004); (Article in Japanese—contains English summary of article).

Crespi, F., et al.; "Near infrared oxymeter prototype for non-invasive analysis of rat brain oxygenation," Optical Sensing, Proceedings of SPIE, vol. 5459, pp. 38-45 (2004).

Yan, Yong-sheng, et al.; "Reduction of motion artifact in pulse oximetry by smoothed pseudo Wigner-Ville distribution," Journal of NeuroEngineering and Rehabilitation, vol. 2, No. 3 (9 pages) (Mar. 2005).

F. Jaillon, et al.; "Diffusing-wave spectroscopy from head-like tissue phantoms: influence of a non-scattering layer," *Optics Express*, vol. 14, No. 22; Oct. 2006, pp. 10181-10194.

G. Dietsche, et al.; "Fiber-based multispeckle detection for time-resolved diffusing-wave spectroscopy: characterization and application to blood flow detection in deep tissue," *Applied Optics*, vol. 46, No. 35; Dec. 2007, pp. 8506-8514.

U.S. Appl. No. 12/563,848, filed Sep. 21, 2009, Youzhi Li.
U.S. Appl. No. 12/570,394, filed Sep. 30, 2009, Clark R. Baker.
U.S. Appl. No. 12/241,160, filed Sep. 30, 2008, Ed McKenna.

* cited by examiner

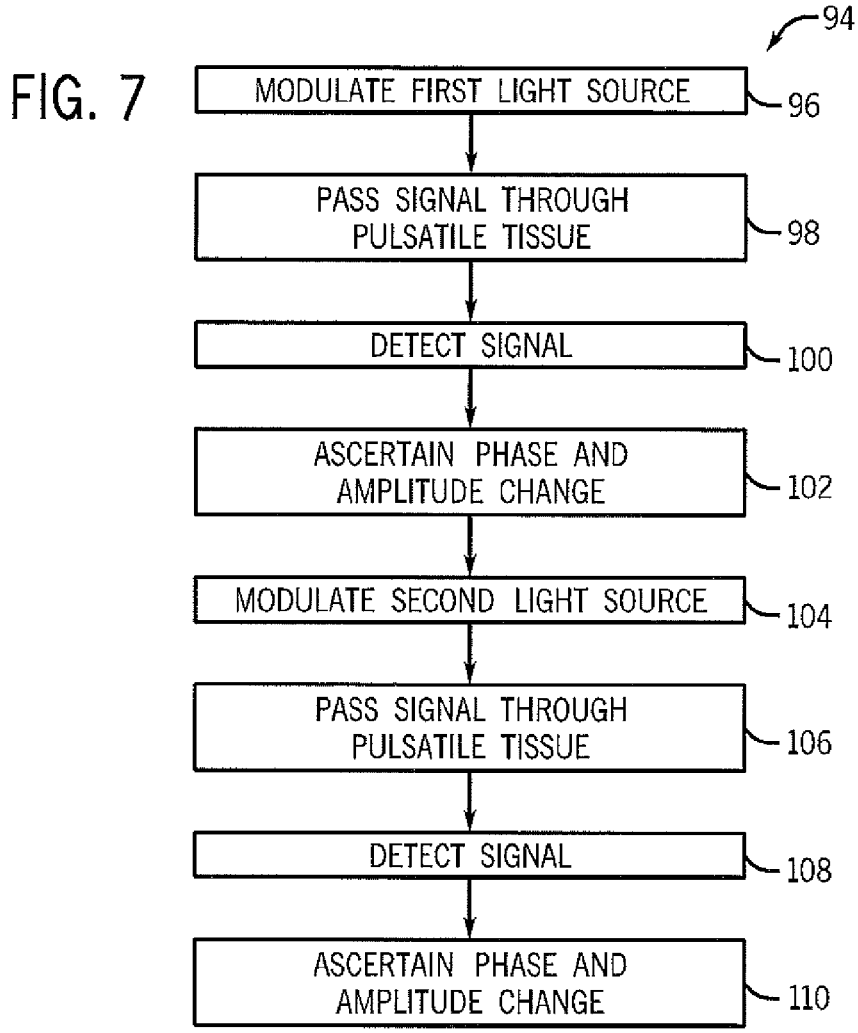
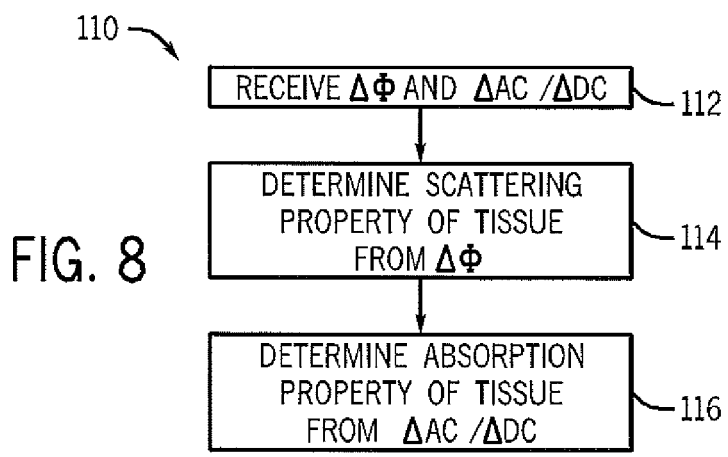

TIME-DIVISION MULTIPLEXING IN A MULTI-WAVELENGTH PHOTON DENSITY WAVE SYSTEM

BACKGROUND

The present disclosure relates generally to non-invasive measurement of physiological parameters and, more particularly, to multi-wavelength photon density wave measurements of physiological parameters.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Pulse oximetry may be defined as a non-invasive technique that facilitates monitoring of a patient's blood flow characteristics. For example, pulse oximetry may be used to measure blood oxygen saturation of hemoglobin in a patient's arterial blood and/or the patient's heart rate. Specifically, these blood flow characteristic measurements may be acquired using a non-invasive sensor that passes light through a portion of a patient's tissue and photo-electrically senses the absorption and scattering of the light through the tissue. Typical pulse oximetry technology may employ two light emitting diodes (LEDs) and a single optical detector to measure pulse and oxygen saturation of a given tissue bed.

A typical signal resulting from the sensed light may be referred to as a plethysmograph waveform. Such measurements are largely based on absorption of emitted light by specific types of blood constituents. Once acquired, this measurement may be used with various algorithms to estimate a relative amount of blood constituent in the tissue. For example, such measurements may provide a ratio of oxygenated hemoglobin to total hemoglobin in the volume being monitored. The amount of arterial blood in the tissue is generally time-varying during a cardiac cycle, which is reflected in the plethysmographic waveform.

The accuracy of blood flow characteristic estimation via pulse oximetry may depend on a number of factors. For example, variations in light absorption characteristics can affect accuracy depending on where the sensor is located and/or the physiology of the patient being monitored. Additionally, various types of noise and interference can create inaccuracies. For example, electrical noise, physiological noise, and other interference can contribute to inaccurate blood flow characteristic estimates.

SUMMARY

Certain aspects commensurate in scope with the originally claimed embodiments are set forth below. It should be understood that these aspects are presented merely to provide the reader with a brief summary of certain forms the embodiments might take and that these aspects are not intended to limit the scope of the presently disclosed subject matter. Indeed, the embodiments may encompass a variety of aspects that may not be set forth below.

Present embodiments relate to multi-wavelength photon density wave medical systems, methods, and devices. In one embodiment, a multi-wavelength system may include a sensor, a sensor cable, and a patient monitor. The sensor may have an emitter output and a detector input configured to pass a multi-wavelength photon density wave input signal into a patient and receive a resulting multi-wavelength photon density wave output signal. The sensor cable may couple to the sensor using two optical cables for transmitting and receiving the multi-wavelength photon density wave signals. The patient monitor may couple to the sensor cable and generate several time-division multiplexed single-wavelength input signals by modulating one or more light sources at a frequency sufficient to produce resolvable photon density waves in the patient. By combining the several time-division multiplexed single-wavelength input signals into one of the optical cables of the sensor cable, the patient monitor may generate the multi-wavelength photon density wave input signal.

BRIEF DESCRIPTION OF THE DRAWINGS

Advantages of the presently disclosed subject matter may become apparent upon reading the following detailed description and upon reference to the drawings in which:

FIG. 7 is a flowchart representing an embodiment of a method for obtaining physiological measurements using the system of FIG. 1, in accordance with an embodiment; and FIG. 8 is a flowchart representing an embodiment of an algorithm for use by the system of FIG. 1 for determining scattering and absorption properties of patient tissue.

DETAILED DESCRIPTION

Figure 1:
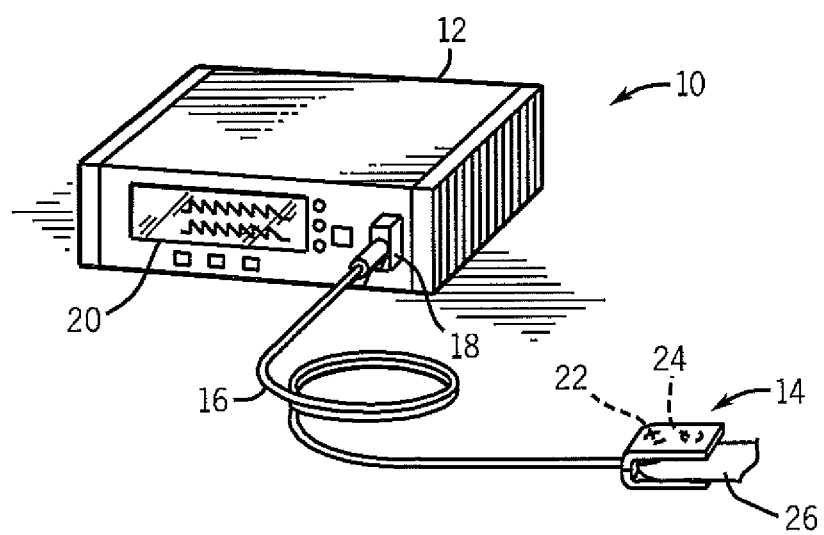
FIG. 1 is a perspective view of a pulse oximeter system in accordance with an embodiment.

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Present embodiments relate to non-invasively measuring physiological parameters corresponding to blood flow in a patient. Specifically, light may be emitted into a patient and photoelectrically detected after having passed through pulsatile patient tissue. Rather than send a light signal modulated at a rate that is effectively DC through the pulsatile patient tissue, present embodiments involve modulating the light at frequencies sufficient to produce waves of photons known as photon density waves in the tissue. The photon density waves may propagate through the pulsatile tissue of the patient, undergoing refraction, diffraction, interference, dispersion, attenuation, and so forth. These effects may vary depending on the current composition of the patient tissue, which in turn may vary as blood enters and exits the tissue.

Multiple photon density wave signals of various wavelengths of light may be time-division multiplexed at a patient monitor into a single emission optical cable and provided to a sensor attached to a patient. Such a multi-wavelength photon density wave signal, emitted into pulsatile patient tissue, may be recovered by the sensor after reflection or transmission through the tissue. Thereafter, a single detection optical cable may carry the received signal to the patient monitor. Since the multi-wavelength photon density wave signal is time-division multiplexed, a single detector may photoelectrically detect and digitize the received signal. The detected and digitized multi-wavelength signal may be demultiplexed into its component single-wavelength signals.

Each of the received and detected single-wavelength photon density wave signals may be analyzed to obtain scattering and absorption properties of the pulsatile patient tissue. In particular, a change in phase of a photon density wave signal passed through the patient tissue may correspond to scattering components of the tissue, while a change in amplitude may correspond to absorptive components in the tissue. For example, since the scattering coefficient may change over time depending on a total quantity of hemoglobin in the tissue, variations in phase changes may correspond to variations in total hemoglobin. Thus, such changes in phase over time may be due predominantly to the total number of scattering particles (e.g., total hemoglobin), and not merely a ratio of particles (e.g., oxygenated and total hemoglobin).

Changes in amplitude of the photon density wave signals may correspond to the absorptive components of the pulsatile patient tissue, not scattering components. Certain components of the tissue may absorb different wavelengths of light, such as red or infrared light, in different amounts. By analyzing decreases in amplitudes of the received single-wavelength photon density wave signals, a ratio of different types of particles in the pulsatile patient tissue, such as oxygenated and deoxygenated hemoglobin, may be estimated. With measurements of scattering and absorption characteristics of the tissue, physiological parameters such as SpO2, regional oxygen saturation, total hemoglobin, perfusion, and many others may be obtained.

With the foregoing in mind, FIG. 1 illustrates a perspective view of a photon density wave pulse oximetry system 10, which may include a patient monitor 12 and a pulse oximeter sensor 14. A sensor cable 16 may connect the patient monitor 12 to the sensor 14, and may include two fiber optic cables. One of the fiber optic cables within the sensor cable 16 may transmit a multi-wavelength photon density wave input signal from the patient monitor 12 to the sensor 14, and another of the fiber optic cables may transmit a multi-wavelength photon density wave output signal from the sensor 14 to the patient monitor 12. The cable 16 may couple to the monitor 12 via an optical connection 18. Based on signals received from the sensor 14, the patient monitor 12 may determine certain physiological parameters that may appear on a display 20. Such parameters may include, for example, a plethysmogram or numerical representations of patient blood flow (e.g., partial oxygen saturation or a measurement of total hemoglobin).

The patient monitor 12 may modulate light sources of two or more wavelengths at modulation frequencies of approximately 50 MHz-3 GHz, which may produce resolvable photon density wave signals in pulsatile tissue because the resulting photon density waves at such frequencies may have wavelengths shorter than a mean absorption distance in pulsatile tissue. In some embodiments, the patient monitor 12 may sweep the modulation frequency of one or more of the light sources in a range from 50 MHz to 2.4 GHz. Some embodiments of the patient monitor 12 may be configured to modulate between 100 MHz and 1 GHz or to sweep a range from 100 MHz to 1 GHz. The patient monitor 12 may, in certain embodiments, modulate the light sources primarily at a frequency of approximately 500 MHz. Examples of such single-wavelength photon density wave signals that may be generated by the patient monitor 12 may be illustrated below with reference to FIGS. 3 and 4.

The patient monitor 12 may time-division multiplex these several single-wavelength photon density wave signals into a single multi-wavelength photon density signal, in which each of the single-wavelength photon density wave signals is alternatingly the sole wavelength active in the multi-wavelength signal for brief periods of time (e.g., approximately 150 ns to several ms). Generally, these periods of time may be brief enough to enable each of the single-wavelength components of the multi-wavelength signal to pass through the pulsatile tissue at substantially the same time. In other words, the periods of time may be brief enough such that, for purposes of pulse oximetry, substantially no perceptible change in the pulsatile tissue of the patient may occur between the start of the first single-wavelength component and the start of the last single-wavelength component in the multi-wavelength signal. An example of such a multi-wavelength signal composed of time-division multiplexed single-wavelength signals may be illustrated below with reference to FIG. 5.

The multi-wavelength signal may be provided to the sensor 14 via the sensor cable 16. The sensor 14 may include an emitter output 22 and a detector input 24. The emitter output 22 may guide the multi-wavelength photon density wave signal from the sensor cable 16 to enter pulsatile tissue of a patient 26. The detector input 24 may receive the resulting multi-wavelength photon density signal from the pulsatile tissue of the patient 26 and guide the received signal back to the patient monitor 12 via the sensor cable 16. The sensor 14 may be, for example, a reflectance-type sensor or a transmission-type sensor.

When the resulting multi-wavelength photon density wave signal reaches the patient monitor 12, the patient monitor 12 may detect and demultiplex the signal into the single-wavelength component signals. Wave characteristics of the received single-wavelength photon density signals may be measured in accordance with present embodiments, and may include characteristics that relate predominantly to absorption of the emitted light in the probed medium (e.g., amplitude change) and characteristics that relate predominantly to scattering in the probed medium (e.g., phase shift). The correlation of certain wave characteristic (e.g., amplitude and phase) measurements to certain medium characteristics (e.g., quantity of scattering particles and blood oxygen saturation) may depend on the modulation of the light sources within the patient monitor, which may generate resolvable photon density waves. Specifically, to produce resolvable photon density waves, the modulation frequency of such signals should produce photon density waves having modulation wavelengths that are shorter than a mean absorption distance of the probed tissue medium.

As indicated above, the system 10 may be utilized to make measurements that relate predominantly to scattering in the observed volume. More specifically, the system 10 may be utilized to make measurements relating to a total amount of scattering particles in the observed volume based on phase shifts detected in the emitted light waves. For example, the system 10 may emit light that is modulated at a frequency (e.g., 50 MHz to 3 GHz) sufficient to generate resolvable photon density waves, and then measure the phase shift of these waves to facilitate estimation of a total number of scattering particles in the observed medium. Similarly, as set forth above, the system 10 may be utilized to make measurements that relate predominantly to absorption in an observed volume. For example, the system 10 may detect changes in AC and DC amplitudes of the resolvable photon density waves to facilitate detection of a ratio of certain constituents in the blood (e.g., a ratio of oxygenated to total hemoglobin). It should be noted that the amplitude changes and phase shifts measured at a detection point may be considered relative to one or more points. For example, the amplitude and phase shifts measured from the detector input 24 may be considered relative to the associated values generated at the emitter output 22.

Figure 2:
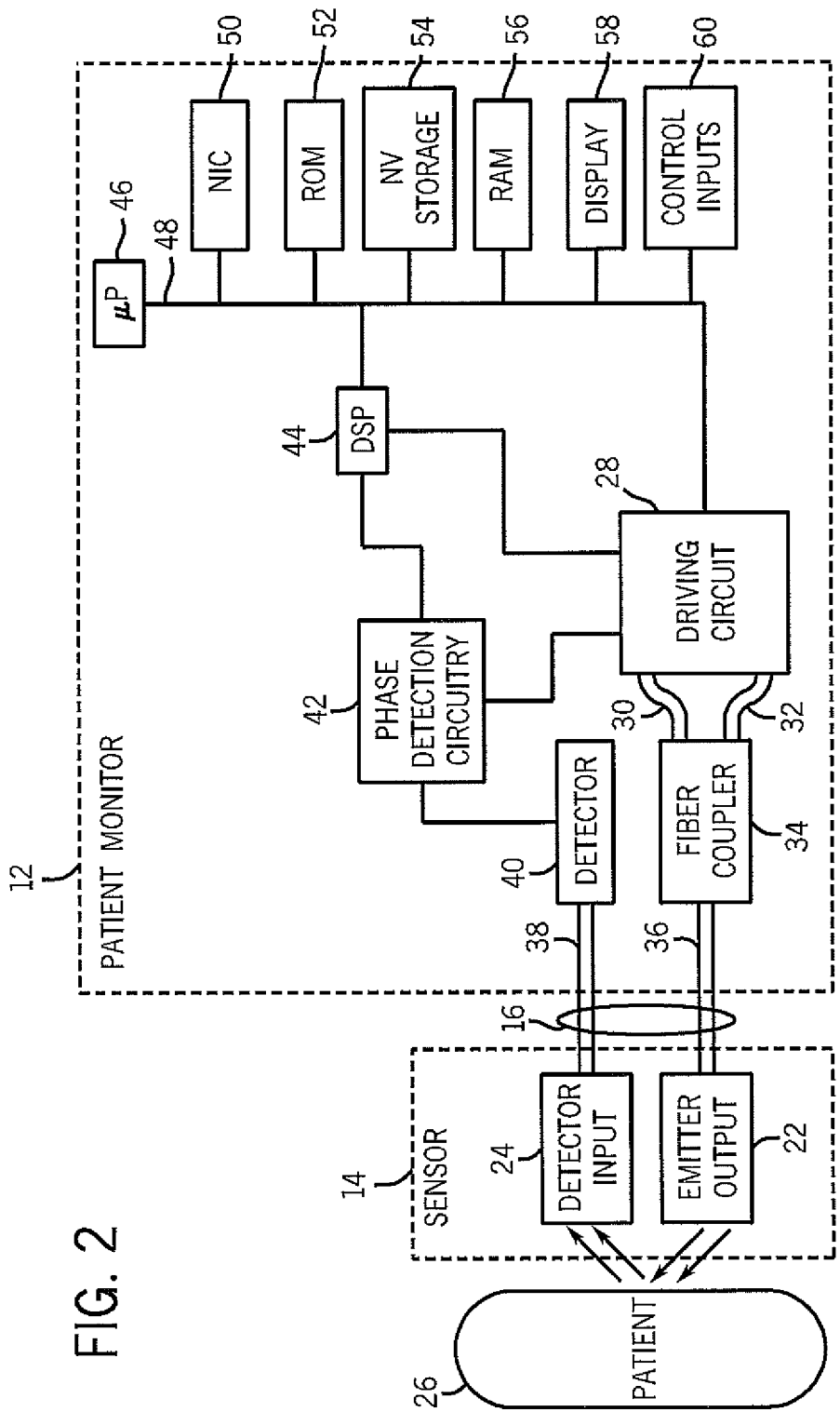
FIG. 2 is a block diagram of the pulse oximeter system of FIG. 1, in accordance with an embodiment.

FIG. 2 represents a block diagram of the system 10 of FIG. 1. As illustrated in FIG. 2, the patient monitor 12 may generate several single-wavelength photon density wave signals at alternating periods of time (e.g., between approximately every 150 ns and several ms) using a driving circuit 28, such that generally only one single-wavelength photon density wave signal is active at any given time. The period of time that each single-wavelength photon density wave is active may be short enough such that only very slight changes occur in patient 26 pulsatile tissue content. In this way, despite that the several single-wavelength photon density wave signals are not active simultaneously, the alternating pulses of the several single-wavelength signals may occur close enough to one another such that, for medical purposes, they occur at substantially the same time.

The driving circuit 28 may include one or more light sources that may emit at least two different wavelengths of light. Such wavelengths may include red wavelengths of between approximately 600-700 nm and/or infrared wavelengths of between approximately 800-1000 nm. By way of example, the light sources of the driving circuit 28 may be laser diodes that emit red or infrared light with wavelengths of approximately 660 nm or 808 nm, respectively. In some embodiments, the one or more light sources of the driving circuit 28 may emit three or more different wavelengths light. Such wavelengths may include a red wavelength of between approximately 620-700 nm (e.g., 660 nm), a far red wavelength of between approximately 690-770 nm (e.g., 730 nm), and an infrared wavelength of between approximately 860-940 nm (e.g., 900 nm). Other wavelengths that may be emitted by the one or more light sources of the driving circuit 28 may include, for example, wavelengths of between approximately 500-600 nm and/or 1000-1100 nm.

The driving circuit 28 may modulate these light sources at a modulation frequency between approximately 50 MHz to 3 GHz. Such modulation frequencies may suffice to produce resolvable photon density waves when emitted into pulsatile tissue of the patient 26, since corresponding wavelengths of the photon density waves may be shorter than a mean distance of absorption in the tissue. The modulation frequency of each light source may vary, as one light source may have a higher or lower modulation frequency than another light source. The driving circuit 28 may represent one or more components of commonly available drive circuits (e.g., DVD R/W driver circuits) for modulation. Examples of such devices may include the LMH6525 device available from National Semiconductor Inc.

In FIG. 2, the driving circuit 28 is illustrated to generate two single-wavelength photon density wave signals of different wavelengths respectively through an optical cable 30 and an optical cable 32. However, it should be appreciated that the driving circuit 28 may be designed to generate any suitable number of single-wavelength signals. A fiber coupler 34 may join the two optical cables 30 and 32 together, multiplexing the two single-wavelength photon density wave signals into one multi-wavelength photon density wave signal. This multi-wavelength photon density wave signal may represent a combination of the several single-wavelength photon density wave signals generated at alternating periods of time by the driving circuit 28 and, as such, may be understood to represent a time-division multiplexed combination of the several single-wavelength photon density wave signals.

An optical cable 36 may carry the multi-wavelength photon density wave signal through the sensor cable 16 to the emitter output 22 of the sensor 14. The multi-wavelength photon density wave signal may thereafter enter pulsatile tissue of the patient 26, where the signal may be scattered and absorbed by various components of the tissue. The detector input 24 may receive and guide the portion of the signals reflected or transmitted through the patient 26 tissue to the patient monitor 12 over an optical cable 38, which may be a second of only two optical cables of the sensor cable 16.

Because the multi-wavelength signal represents a time-division multiplexed combination of the several single-wavelength photon density wave signals, only one of the single-wavelength signals generally may pass through the patient 26 and the optical cable 38 at any given time. As such, the received multi-wavelength photon density wave generally may be photoelectrically detected in a single photodetector 40, which may receive and convert the optical signal to an electrical signal, before amplifying the received signal. In certain embodiments involving more than two single-wavelength signals, two or more single-wavelength signals may be passed through the patient 26 at once and wavelength demultiplexed before the overall multi-wavelength photon density wave signal may be time-division demultiplexed.

The resulting signal may enter phase detection circuitry 42, and the output of the phase detection circuitry 42 may be digitized and entered into a processor, such as a digital signal processor (DSP) 44, to be analyzed for phase and amplitude changes. To distinguish between the various single-wavelength signals of the multi-wavelength signal, the driving circuit 28 may provide the phase detection circuitry 42 and the DSP 46 with time-division information to indicate which single-wavelength photon density wave signal is currently being received. Using such time-division information, the phase detection circuitry 42 and the DSP 46 may demultiplex the time-division multiplexed multi-wavelength photon density wave signal into its component single-wavelength signal segments.

By analyzing changes in amplitude and phase between the received single-wavelength photon density wave signals and corresponding emitted single-wavelength photon density wave signals of a particular wavelength of light, absorption and scattering properties of the patient 26 tissue for that wavelength of light may be determined. To obtain phase changes corresponding to scattering in the patient 26 tissue, the phase detection circuitry 42 may obtain the received multi-wavelength photon density wave signal from the detector 40, and time-division information, clock signals, and/or reference signals relating to the corresponding original emitted single-wavelength photon density wave signals from the driving circuitry 28. The phase detection circuitry 42 may thereafter detect phase changes between the original emitted signal and the received signal associated with each wavelength. In certain embodiments, the phase detection circuitry 42 and the driving circuit 28 may be individual components of a single semiconductor device, such as a DVD R/W driver circuit. Such devices may include the LMH6525 device available from National Semiconductor Inc.

The DSP 44 may receive the output from the phase detection circuitry 42 and time-division information and/or reference signal information from the driver circuit 28. By comparing amplitude changes between the received photon density wave signals and the corresponding emitted photon density wave signals of the same corresponding wavelength of light, absorption properties of the patient 26 tissue for each wavelength of light may be determined. Using the absorption and scattering information associated with the amplitude changes and phase changes of the photon density wave signals passed through the patient 26, the DSP 44 may determine a variety of properties based on algorithms stored in memory on the DSP 44 or received from external sources, such as a microprocessor 46 or other devices via a bus 48. One example of such an algorithm may be described below with reference to FIG. 8.

In general, the DSP 44 may ascertain certain properties of the patient 26 tissue based on the following relationships described below. For a modulation frequency where the product of the frequency and the mean time between absorption events is much larger than 1, the change in phase $\Delta\phi$ between two points located a distance r from each other on a tissue bed may be given by the following relation:

$$\Delta\phi = r\sqrt{\frac{\omega\mu'_s}{6c}}, \tag{1}$$

where c is the speed of light, $\omega$ is the angular frequency of modulation, and $\mu'_s$ is the reduced scattering coefficient. The reduced scattering coefficient for a tissue bed accounts for both blood and surrounding tissue components. This can be written as:

$$\mu'_{s\_total} = V_{blood}\mu'_{s\_blood} + V_{tissue}\mu'_{s\_tissue} \tag{2}.$$

The time varying component of this equation at a single wavelength will generally be only the portion due to arterial blood. The time varying component of this equation at a second wavelength will allow for the deconvolution of the scattering coefficient. The scattering coefficient for blood is related to the hematocrit (HCT) through the following relation:

$$\mu'_{s\_blood} = \sigma_s(1-g)(HCT/V_i)(1-HCT)(1.4-HCT) \tag{3},$$

where g is the anisotropy factor, $\sigma$ is the scattering cross section of an erythrocyte, Vi is the volume of an erythrocyte and HCT is the hematocrit.

As indicated above, the phase of the photon density waves may be sensitive to changes in the scattering coefficient, while the amplitude of the photon density waves may be sensitive to the concentration of absorbers in the medium. Specifically, with regard to amplitude measurements, the AC amplitude and DC amplitude may yield information about absorption in the volume. Thus, detection of amplitude changes in the photon density waves may be utilized to calculate absorber concentration values in the observed medium, such as blood oxygen saturation values. Such calculations may be made using a standard ratio of ratios (e.g., ratrat) technique for the constant and modulated values of the photon density wave amplitudes at two wavelengths. Once the ratio of ratios values is obtained, it may be mapped to the saturation from clinical calibration curves. In general, the amplitude of the resulting photon density waves after passing through the patient 26 tissue may be described as follows:

$$A = \frac{A_0}{4\pi D r_{sd}} \exp\left[-r_{sd}\sqrt{\frac{[(\mu_a c)^2 + \omega^2]^{\frac{1}{2}} + \mu_a c}{2D}}\right], \tag{4}$$

where $A_0$ is the initial amplitude, D is the diffusion coefficient given as $$D = \frac{c}{3(\mu'_s + \mu_a)}, \mu_a$$

is the absorption coefficient, and $r_{sd}$ is the distance between the emitter and the detector.

With regard to phase shift measurements, when the wavelength of the photon density waves is less than a mean absorption distance of the pulsatile tissue of the patient 26, the phase becomes almost exclusively a function of the scattering coefficient. While dependent upon the tissue bed being probed, this is generally believed to occur at a modulation frequency in the range of approximately 500 MHz. Thus, the phase shift measurement may yield information about the number of erythrocytes or red blood cells in the local probed volume. The HCT discussed above is proportional to the number of erythrocytes. Accordingly, by sweeping frequencies, a multi-parameter output may be obtained that relates to standard pulse oximetry measurements as well as the puddle hematocrit. In general, the change in phase of the resulting photon density waves after passing through the patient 26 tissue may be described as follows:

$$\Delta\Phi = r_{sd}\sqrt{\frac{[(\mu_a c)^2 + \omega^2]^{\frac{1}{2}} - \mu_a c}{D}} + \Phi_0, \tag{5}$$

where $\Phi_0$ is a constant.

The amplitude and phase at a given frequency may be proportional to the scattering and absorption coefficient at a given wavelength until the product of the frequency and the mean time between absorption events is much larger than 1. When the product of the frequency and the mean time between absorption events is much larger than 1, the amplitude is a function of the absorption and phase is only a function of the scattering. Thus, in some embodiments, the driving circuit 28 may perform a frequency sweep over time (e.g., from 100 MHz to 1 GHz) to reduce the error in the determination of a single value of reduced scattering coefficient for the blood and a single value of absorption coefficient.

In some embodiments, by modulating the light sources at a sufficient frequency, and, thus, facilitating a detectable phase shift that corresponds to scattering particles, present embodiments may provide an extra degree of certainty for blood flow parameter measurements. Indeed, the detected amplitude for the photon density waves may be utilized to calculate traditional pulse oximetry information and the phase may be utilized to confirm that such values are correct (e.g., within a certain range of error). For example, the amplitude information may be utilized to calculate a blood oxygen saturation ($SpO_2$) value and empirical data may indicate that a particular SpO$_2$ value should correspond to a particular phase variation at a given frequency. In other words, there may be a certain phase change that should accompany a given increase in absorber observed as a change in amplitude. Various known techniques (e.g., learning based algorithms such as support vector machines, cluster analysis, neural networks, and PCA) based on the measured phase shift and amplitude change may be compared to determine if the amplitude shift and phase shift correlate to a known SpO$_2$. If both the measured amplitude shift and phase shift correlate to a known SpO$_2$, the measured SpO$_2$ value may be deemed appropriate and displayed or utilized as a correct SpO$_2$ value. Alternatively, if the measured amplitude shift and phase shift do not agree, the calculated SpO$_2$ value may be identified as being corrupt or including too much noise and, thus, may be discarded.

As shown in FIG. 2, the patient monitor 12 may include a general- or special-purpose microprocessor 46 on the bus 48, which may govern other general operations of the patient monitor 12, such as how data from the DSP 44 is employed by other components on the bus 48. A network interface card (NIC) 50 may enable the patient monitor 12 to communicate with external devices on a network. A read only memory (ROM) 52 may store certain algorithms, such as those used by the DSP 44 to determine absorption and scattering properties of the patient 26 tissue, and nonvolatile storage 54 may store longer long-term data. Additionally or alternatively the nonvolatile storage 54 may also store the algorithms for determining tissue properties.

Other components of the patient monitor 12 may include random access memory (RAM) 56, a display interface 58, and control inputs 60. The RAM 56 may provide temporary storage of variables and other data employed while carry out certain techniques described herein, while the display interface 58 may allow physiological parameters obtained by the patient monitor 12 to appear on the display 20. The control inputs 60 may enable a physician or other medical practitioner to vary the operation of the patient monitor 12. By way of example, a practitioner may select whether the patient 26 is an adult or neonate, and/or whether the tissue is high perfusion or low perfusion tissue. Such a selection with the control inputs 60 may vary the modulation frequency of one or more of the single-wavelength photon density wave signals, may disable one or more of the single-wavelength photon density wave signals, or may cause a preprogrammed sequence of operation, such as a sweep of modulation frequencies for one or more of the single-wavelength photon density wave signals, to begin.

Figure 3:
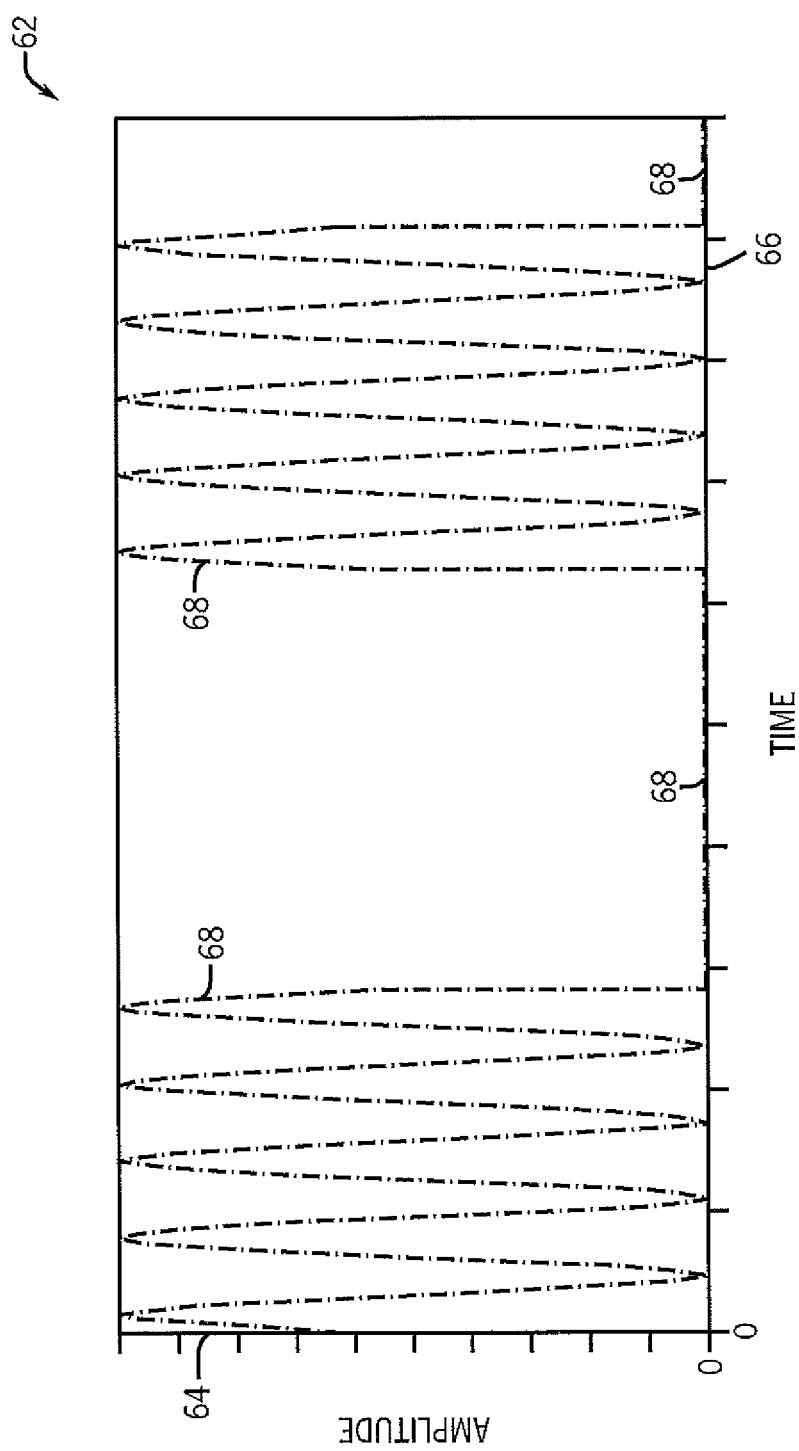
FIG. 3 is a plot of a first single-wavelength photon density wave signal for use in the system of FIG. 1, in accordance with an embodiment.

As noted above, the driving circuit 28 may emit several single-wavelength photon density wave signals that may be combined in the fiber coupler 34 into one multi-wavelength photon density wave signal and sent to the sensor 14. Turning to FIG. 3, a plot 62 may describe an embodiment of one single-wavelength component of such a multi-wavelength photon density wave signal. In the plot 62, an ordinate 64 represents relative amplitude, and an abscissa 66 represents relative time. Numeral 68 refers to a first single-wavelength photon density wave signal (e.g., a 660 nm photon density wave signal) generated by the driving circuit 28. It should be understood that the signal 68 may alternatively have a different amplitude, modulation frequency, and/or phase.

The single-wavelength signal 68 may be active at regular intervals for a given period of time (e.g., between approximately 150 ns and 1 ms) for time-division multiplexing with one or more other signals. As noted below with reference to FIGS. 4 and 5, the single-wavelength photon density wave signal 68 may be combined with other single-wavelength signals into a multi-wavelength signal. The driving circuit 28 may thus emit the signal 68 at intervals and for periods of time related to the number of other emitted single-wavelength signals to be combined into the multi-wavelength signal. For example, if the single-wavelength photon density wave signal 68 is one of two single-wavelength photon density wave signals emitted by the driving circuit 28, the signal 68 may be emitted by the driving circuit 28 approximately half of the time, as shown in the plot 62.

Figure 4:
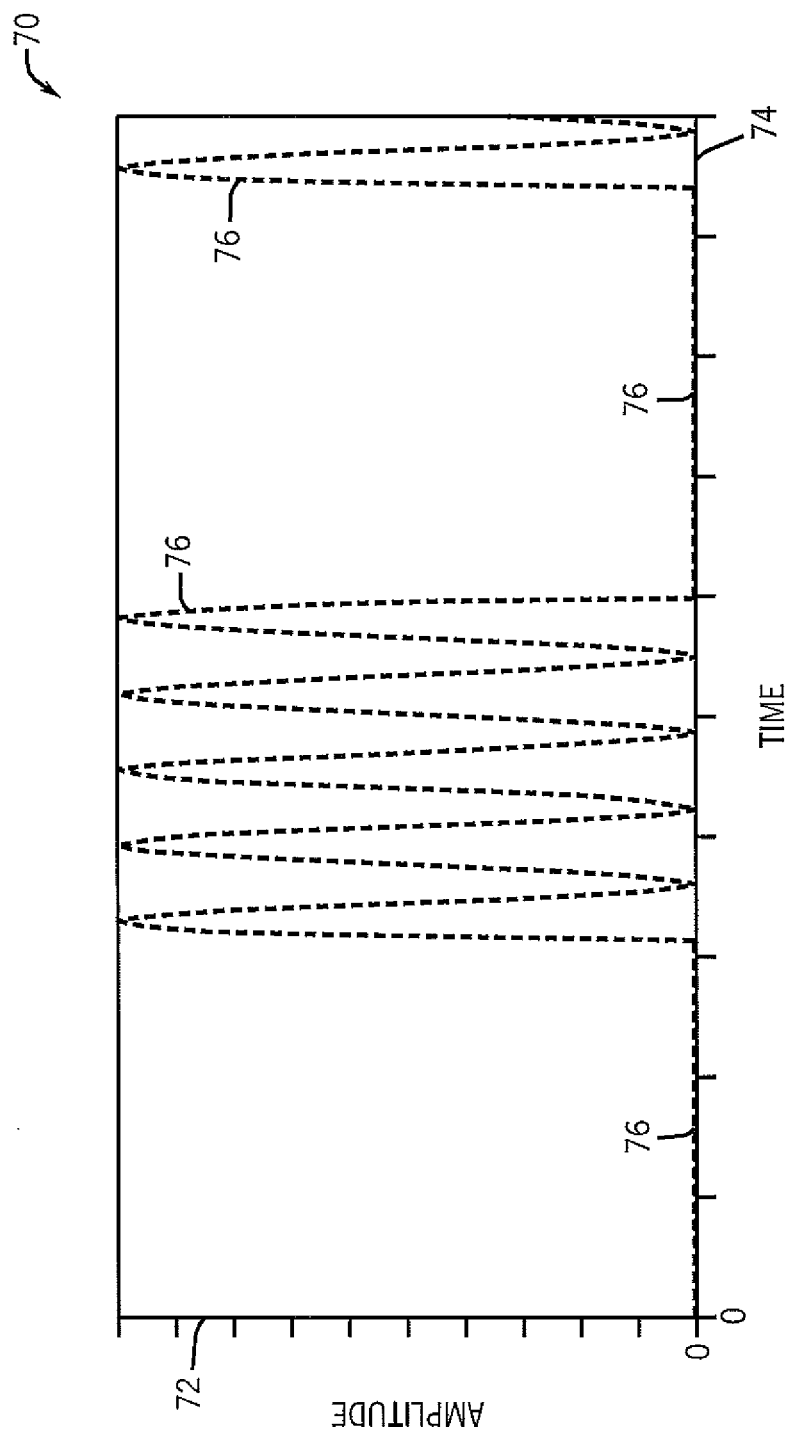
FIG. 4 is a plot of a second single-wavelength photon density wave signal for use in the system of FIG. 1, in accordance with an embodiment.

FIG. 4 is a plot 70 that may describe an embodiment of another single-wavelength component of a multi-wavelength photon density wave signal. In the plot 70, an ordinate 72 represents relative amplitude, and an abscissa 74 represents relative time. Numeral 76 refers to a second single-wavelength photon density wave signal (e.g., an 808 nm photon density wave signal) generated by the driving circuit 28. The single-wavelength signal 76 may be active at regular intervals for a given period of time (e.g., between approximately 150 ns and 1 ms) for time-division multiplexing with one or more other photon density wave signals, such as the single-wavelength photon density wave signal 68. In particular, the signal 76 may be active at times when the signal 68 of the plot 62 is not. It should be understood that the signal 76 may alternatively have a different amplitude, modulation frequency, and/or phase.

Figure 5:
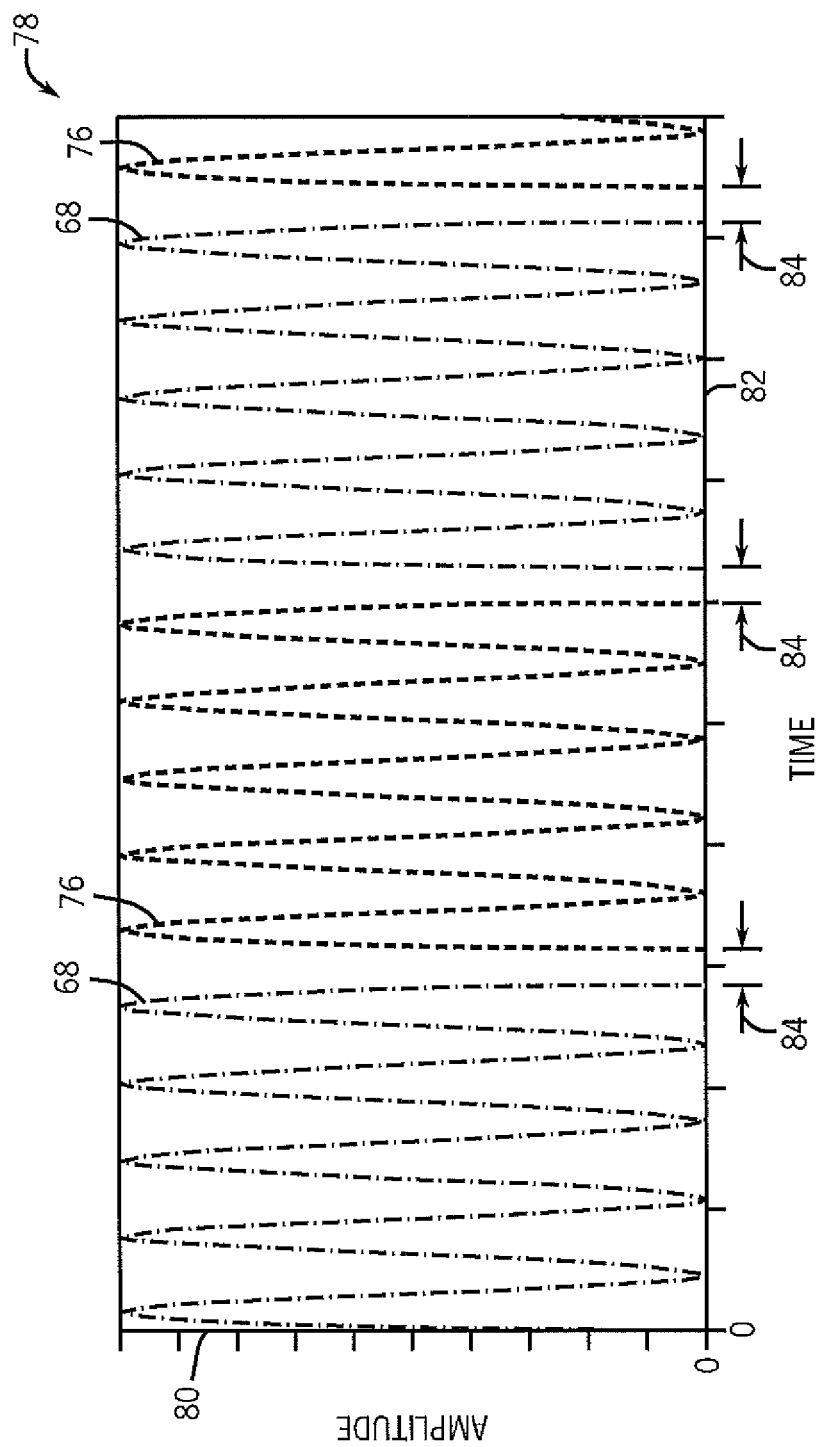
FIG. 5 is a plot of a multi-wavelength photon density wave signal combining the first and second single-wavelength photon density wave signals of FIGS. 3 and 4, in accordance with an embodiment.

The single-wavelength photon density wave signals 68 and 76 emitted by the driving circuitry 28 may be combined into a single multi-wavelength photon density wave signal in the fiber coupler 38. FIG. 5 represents a plot 78 illustrating such a multi-wavelength photon density wave signal having time-division multiplexed single-wavelength component signals 68 and 76. In the plot 78, an ordinate 80 represents relative amplitude, and an abscissa 82 represents relative time. The signals 68 and 76 may occur at different, non-overlapping, times in the multi-wavelength signal of the plot 78. In this way, the two single-wavelength photon density wave signals 68 and 76 may be later separated into distinct single-wavelength signals with time-division demultiplexing of the plot 78. Although not necessary, a brief dark period 84 (e.g., 3 ns) may separate the two signals 68 and 76.

When the multi-wavelength photon density wave signal of the plot 78 has passed through the pulsatile tissue of the patient 26, single-wavelength component output signals, resulting from the signals 68 and 76, may be isolated in the phase detection circuitry 42 and the DSP 44 with time-division information the driving circuit 28. Comparing one of the single-wavelength output signals with the corresponding original single-wavelength signal 68 or 76 of the plot 78 may indicate various properties of the patient 26 tissue.

Figure 6:
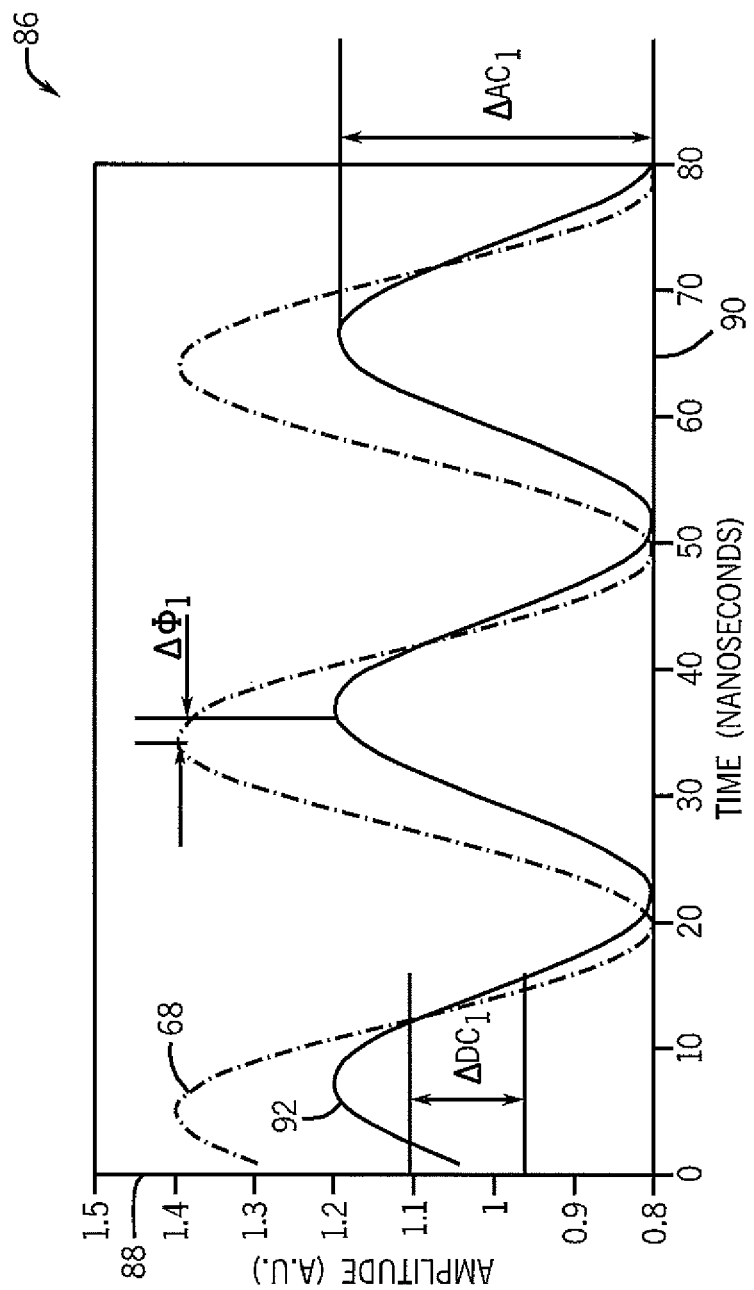
FIG. 6 is a plot representing a comparison between a portion of the multi-wavelength photon density wave signal of FIG. 5 and a received single-wavelength photon density wave signal after the signal of FIG. 5 has been passed through a patient, in accordance with an embodiment.

For example, FIG. 6 illustrates the superimposition of a single-wavelength segment of the signal 68 from the multi-wavelength plot 78 with the resulting single-wavelength signal detected after passage through the patient 26. Like the plots 62, 70, and 78 of FIGS. 3-5, plot 86 of FIG. 6 includes an ordinate 88 representing relative amplitude and an abscissa 90 representing time in units of nanoseconds (ns). The input single-wavelength photon density wave signal 68 and a corresponding output single-wavelength photon density wave signal 80 may have a DC amplitude difference of $\Delta DC_1$, an AC amplitude difference of $\Delta AC_1$, and a phase difference of $\Delta \phi_1$. The amplitude measurements $\Delta DC_1$ and $\Delta AC_1$ may correspond essentially only to absorption in the patient 26 tissue, while the phase difference $\Delta \phi_1$ may correspond essentially only to scattering in the patient 26 tissue, as generally described with reference to FIG. 8 below.

Since another single-wavelength photon density wave signal, such as the single-wavelength signal 76, may occur very shortly thereafter, performing a similar comparison with the other single-wavelength signal may yield additional measurements for absorption and scattering properties of the patient 26 for the second wavelength, at substantially the same time. Thus, the patient monitor 12 may determine at least four measurements associated with properties of the patient 26 tissue for substantially the same time for medical purposes associated with pulse oximetry, including two absorption and two scattering properties. In other words, because substantially no perceptible change in the pulsatile tissue of the patient may occur between the start of the first single-wavelength signal 68 and the start of the second single-wavelength signal 76, for purposes of pulse oximetry, the four measurements may be understood to occur at substantially the same time.

FIG. 7 illustrates a flowchart 94, which represents an embodiment of a method for performing photon density wave measurements using two wavelengths of light. In a first step 96, the driving circuit 28 may modulate a light source emitting a first wavelength (e.g., a 660 nm wavelength) at a modulation frequency sufficient to produce resolvable photon density waves within the patient 26 for a brief period of time (e.g., between approximately 150 ns and 1 ms). The period of time may depend, for example, on the modulation frequency or the number of wavelengths of light that the driving circuit 28 will modulate. Generally, the modulation frequency may result in a photon density wave wavelength shorter than a mean absorption distance of the pulsatile tissue of the patient 26. In other words, such modulation frequency may exceed the product of the mean absorption coefficient multiplied by the speed of light. Thus, depending on the patient 26, the modulation frequency may be between 50 MHz to 3 GHz. In some embodiments, the light source may be modulated at a frequency of approximately 500 MHz.

In step 98, the first single-wavelength photon density wave signal may enter the fiber coupler 34 before being transmitted to the sensor 14 via the optical cable 36. Only the first single-wavelength signal may travel across the optical cable 36 at this time. The first single-wavelength photon density wave signal may enter pulsatile tissue of the patient 26 through the emitter output 22 of the sensor 14. After the signal has been reflected or transmitted through the patient 26 tissue, the detector input 24 of the sensor 14 may receive and guide the signal to the optical cable 38, which may transmit the signal back to the patient monitor 12.

The output single-wavelength photon density wave signal that results when the first single-wavelength photon density wave signal is passed through the patient 26 may be detected in the detector 40 in step 100. In step 102, the phase detection circuitry 44 may determine phase changes between the output single-wavelength photon density wave signal and the corresponding input single-wavelength photon density wave signal, and the DSP 46 may determine amplitude changes. The DSP 46 and/or microprocessor 48 may thereafter determine various scattering and absorption properties of the patient 26 tissue, since changes in phase may correspond to scattering in the patient 26 tissue, while changes in amplitude may correspond to absorption. It should be appreciated that step 102 may occur any time after steps 96-100, including concurrently with or after steps 104-108 described below.

Step 104 may generally begin substantially immediately after step 100. In step 104, the driving circuit 28 may modulate a light source emitting a second wavelength in substantially the same manner as in step 96 to produce a second single-wavelength photon density wave signal. In step 106, the second single-wavelength photon density wave signal may be passed through the patient 26, and in step 108, the output second single-wavelength photon density wave signal may be detected in the detector 40. Step 110 may involve ascertaining phase and amplitude changes between the output second single-wavelength photon density wave signal and the corresponding input single-wavelength photon density wave signal in substantially the same manner as step 102. Step 110 may occur time after steps 104-108.

The flowchart 94 may repeat indefinitely, with step 96 generally beginning after step 108. As the flowchart 94 repeats, the modulation frequency may or may not vary among the light sources and may or may not vary over time. Because both the first and second single-wavelength signals may travel across the optical cable 36, but at distinct times, the two signals of different wavelengths may be understood to be time-division multiplexed and may be understood collectively to form a multi-wavelength photon density wave signal.

FIG. 8 is a flowchart 110, which represents an algorithm that may be used by a processor, such as the DSP 44 of the patient monitor 12, to determine physiological properties of the patient 26 tissue using values obtained by passing a multi-wavelength photon density wave signal through the patient 26 tissue. As such, it should be understood that the flowchart 110 may generally begin after all or part of the flowchart 94 of FIG. 7 has been carried out. In a first step 112, phase change $\Delta\phi_1$ and/or amplitude change $\Delta DC_1$ and/or $\Delta AC_1$ values for one of the single-wavelength components of the multi-wavelength photon density wave signal may be received into or determined by a processor, such as the DSP 44.

In step 114, the DSP 44 may determine a scattering property of the patient 26 tissue for the moment in time at which the single-wavelength component of the multi-wavelength photon density wave signal has passed through the pulsatile tissue of the patient 26. Generally, the scattering property may be represented by a scattering coefficient, and may be determined based on the phase change $\Delta\phi_1$ value obtained in step 112 by using Equation (1).

In step 116, the DSP 44 may determine an absorption property of the patient 26 tissue for the moment in time at which the single-wavelength component of the multi-wavelength photon density wave signal has passed through the pulsatile tissue of the patient 26. Generally, the absorption property may be represented by an absorption coefficient, and may be determined based on the amplitude change $\Delta DC_1$ and/or $\Delta AC_1$ values obtained in step 112 by using Equations (1) and (4).

While the embodiments set forth in the present disclosure may be susceptible to various modifications and alternative forms, specific embodiments have been shown by way of example in the drawings and have been described in detail herein. However, it should be understood that the disclosure is not intended to be limited to the particular forms disclosed. The disclosure is to cover all modifications, equivalents, and alternatives falling within the spirit and scope of the disclosure as defined by the following appended claims.

What is claimed is:

1. A system comprising:
a patient monitor configured to generate a multi-wavelength photon density wave input signal from two or more single-wavelength photon density wave signals generated by a driving circuit configured to modulate one or more light sources at one or more modulation frequencies that exceed the product of a mean absorption coefficient of the pulsatile tissue of the patient multiplied by the speed of light and are sufficient to produce resolvable photon density waves in the pulsatile tissue of the patient, in which each of the single-wavelength photon density wave signals is alternatingly the sole wavelength active in the multi-wavelength photon density wave input signal for periods of time brief enough to enable each of the single-wavelength photon density wave signals to pass through pulsatile tissue of a patient such that there is no perceptible change in the pulsatile tissue of the patient between the start of each of the multi-wavelength photon density wave input signals and the start of each subsequent multi-wavelength photon density wave input signal, wherein the patient monitor is configured to receive a multi-wavelength photon density wave output signal resulting after the multi-wavelength photon density wave input signal is passed through the pulsatile tissue of the patient, and wherein the patient monitor comprises data processing circuitry configured to determine a scattering property and an absorption property of the pulsatile tissue of the patient based at least in part on a comparison between the multi-wavelength photon density wave output signal and the multi-wavelength photon density wave input signal, wherein the mean absorption coefficient is determined based on the absorption property of the pulsatile tissue of the patient;

a sensor having an emitter output and a detector input, wherein the emitter output is configured to pass the multi-wavelength photon density wave input signal into the pulsatile tissue of the patient, and wherein the detector input is configured to receive the multi-wavelength photon density wave output signal from the pulsatile tissue of the patient; and a sensor cable coupled to the sensor and to the patient monitor and having a first optical cable configured to transmit the multi-wavelength photon density wave input signal from the patient monitor to the sensor and having a second optical cable configured to transmit the multi-wavelength photon density wave output signal from the sensor to the patient monitor.

2. The system of claim 1, wherein the sensor is a transmission-type sensor, a reflectance-type sensor, and/or a combination thereof.

3. The system of claim 1, wherein the sensor cable comprises no more than two optical cables.

4. The system of claim 1, wherein the periods of time range from approximately 150 nanoseconds to approximately 1 millisecond.

5. The system of claim 1, wherein the one or more light sources comprise a red light source and/or an infrared light source and/or a near infrared light source, or any combination thereof.

6. The system of claim 1, wherein the patient monitor is configured to generate the multi-wavelength photon density wave input signal by time-division multiplexing the two or more single-wavelength photon density wave input signals.

7. The system of claim 6, wherein the patient monitor is configured to time-division demultiplex the multi-wavelength photon density wave output signal to obtain a plurality of single-wavelength photon density wave output signals that corresponds respectively to the plurality of time-division multiplexed single-wavelength photon density wave input signals.

8. The system of claim 7, wherein the patient monitor is configured to determine a physiological parameter of the patient based at least in part on a comparison of one of the plurality of single-wavelength photon density wave output signals to a corresponding one of the plurality of time-division multiplexed single-wavelength photon density wave input signals.

9. The system of claim 7, wherein the patient monitor is configured to determine a physiological parameter of the patient based at least in part on a change in phase between one of the plurality of single-wavelength photon density wave output signals and a corresponding one of the plurality of time-division multiplexed single-wavelength photon density wave input signals.

10. The system of claim 7, wherein the patient monitor is configured to determine a physiological parameter of the patient based at least in part on a change in amplitude between one of the plurality of single-wavelength photon density wave output signals and a corresponding one of the plurality of time-division multiplexed single-wavelength photon density wave input signals.

11. A patient monitor comprising:
one or more light sources configured to emit a plurality of wavelengths of light;
a driving circuit configured to modulate the one or more light sources at one or more modulation frequencies that exceed the product of a mean absorption coefficient of a pulsatile tissue of the patient multiplied by the speed of light and are sufficient to produce resolvable photon density waves in the pulsatile tissue of the patient to produce a plurality of single-wavelength photon density wave input signals at non-overlapping intervals;
a fiber coupler configured to combine the plurality of single-wavelength photon density wave input signals into a multi-wavelength photon density wave input signal in which each of the single-wavelength photon density wave signals is alternatingly the sole wavelength active in the multi-wavelength photon density wave input signal for periods of time brief enough to enable each of the single-wavelength photon density wave signals to pass through pulsatile tissue of the patient such that there is no perceptible change in the pulsatile tissue of the patient between the start of each of the multi-wavelength photon density wave input signals and the start of each subsequent multi-wavelength photon density wave input signal;
a sensor cable connector configured to provide the multi-wavelength photon density wave input signal to a first optical cable of a medical sensor configured to be attached to the patient and to receive a multi-wavelength photon density wave output signal from a second optical cable of the medical sensor; and
data processing circuitry configured to time-division demultiplex the multi-wavelength photon density wave output signal into a plurality of single-wavelength photon density wave output signals and to determine a physiological parameter of the patient based at least in part on a comparison of one of the plurality of single-wavelength photon density wave output signals to a corresponding one of the plurality of single-wavelength photon density wave input signals, wherein the data processing circuitry is further configured to determine an absorption property of the patient based at least in part on a change in amplitude between the one of the plurality of single-wavelength photon density wave output signals and the corresponding one of the plurality of single-wavelength photon density wave input signals, and to determine the mean absorption coefficient based on the determined absorption property.

12. The patient monitor of claim 11, wherein the one or more light sources comprise one or more laser diodes.

13. The patient monitor of claim 11, wherein the driving circuit is configured to modulate the one or more light sources at modulation frequencies between 50 MHz and 3 GHz.

14. The patient monitor of claim 11, wherein the driving circuit is configured to modulate the one or more light sources such that each of the plurality of single-wavelength photon density wave input signals has a different respective modulation frequency.

15. The patient monitor of claim 11, wherein the data processing circuitry is configured to determine a scattering property of the patient based at least in part on a change in phase between the one of the plurality of single-wavelength output photon density wave signals and the corresponding one of the plurality of single-wavelength input photon density wave signals.

16. A method comprising:
generating a first photon density wave signal by modulating a light source of a first wavelength using a driving circuit at a frequency that exceeds the product of a mean absorption coefficient of a pulsatile tissue of the patient multiplied by the speed of light;
generating a second photon density wave signal by modulating a light source of a second wavelength at the modulation frequency that exceeds the product of the mean absorption coefficient of the pulsatile tissue of the patient multiplied by the speed of light by using the driving circuit;
combining, using a fiber coupler, the first photon density wave signal and the second photon density wave signal into a multi-wavelength photon density wave input signal in which each of the first and second photon density wave signals is alternatingly the sole wavelength active in the multi-wavelength photon density wave input signal for periods of time brief enough to enable each of the first and second photon density wave signals to pass through pulsatile tissue of a patient such that there is no perceptible change in the pulsatile tissue of the patient between the start of each of the multi-wavelength photon density wave input signals and the start of each subsequent multi-wavelength photon density wave input signal;
emitting the multi-wavelength photon density wave input signal through the pulsatile tissue of the patient for a period of time using a sensor coupled to an input optical cable and attached to the patient;
receiving a multi-wavelength photon density wave output signal that results when the multi-wavelength photon density wave input signal is emitted through the pulsatile tissue of the patient into an output optical cable using the sensor attached to the patient;
determining an absorption property of the pulsatile tissue of the patient based at least in part on a comparison between the multi-wavelength photon density wave output signal and the multi-wavelength photon density wave input signal; and
determining the mean absorption coefficient of the pulsatile tissue of the patient based on the determined absorption property.

17. The method of claim 16, comprising determining a scattering property of the pulsatile tissue of the patient based at least in part on a comparison between the multi-wavelength photon density wave output signal and the multi-wavelength photon density wave input signal.

18. The method of claiml 16, wherein the first photon density wave signal and the second photon density wave signal are combined into the multi-wavelength photon density wave input signal via time-division multiplexing.

19. The method of claim 16, comprising time-division demultiplexing the multi-wavelength photon density wave output signal to obtain first and second single-wavelength photon density output signals that respectively correspond to the first and second time-division multiplexed single-wavelength photon density wave input signals.

* * * * *